US008529432B1

(12) United States Patent
Joh

(10) Patent No.: US 8,529,432 B1
(45) Date of Patent: Sep. 10, 2013

(54) PENILE IMPLANT FOR AIDING ACHIEVEMENT OF A PENILE ERECTION

(71) Applicant: William Kyungha Joh, West Bloomfield, MI (US)

(72) Inventor: William Kyungha Joh, West Bloomfield, MI (US)

(*) Notice: Subject to any disclaimer, the term of this patent is extended or adjusted under 35 U.S.C. 154(b) by 0 days.

(21) Appl. No.: 13/769,815

(22) Filed: Feb. 18, 2013

(51) Int. Cl.
*A61F 5/00* (2006.01)
(52) U.S. Cl.
USPC ............................................. 600/40
(58) Field of Classification Search
USPC .................................. 600/38–41; 623/11.11
See application file for complete search history.

(56) References Cited

U.S. PATENT DOCUMENTS

| 4,807,608 A * | 2/1989 | Levius | 600/40 |
| 5,230,694 A * | 7/1993 | Rosenblum | 600/40 |

* cited by examiner

*Primary Examiner* — John Lacyk
(74) *Attorney, Agent, or Firm* — Michael D. Eisenberg

(57) ABSTRACT

A device configured for being implanted in a male patient's body for assisting the patient to achieve an erection. The device includes at least two rods and an interconnecting structure. The rods can be selectively deployed to the penis shaft when an erection is to be achieved and retracted away from the penis shaft when the patient does not need to achieve an erection. The interconnecting structure is joined to the rods and is configured to stabilize the rods while the rods are in the penis shaft.

23 Claims, 14 Drawing Sheets

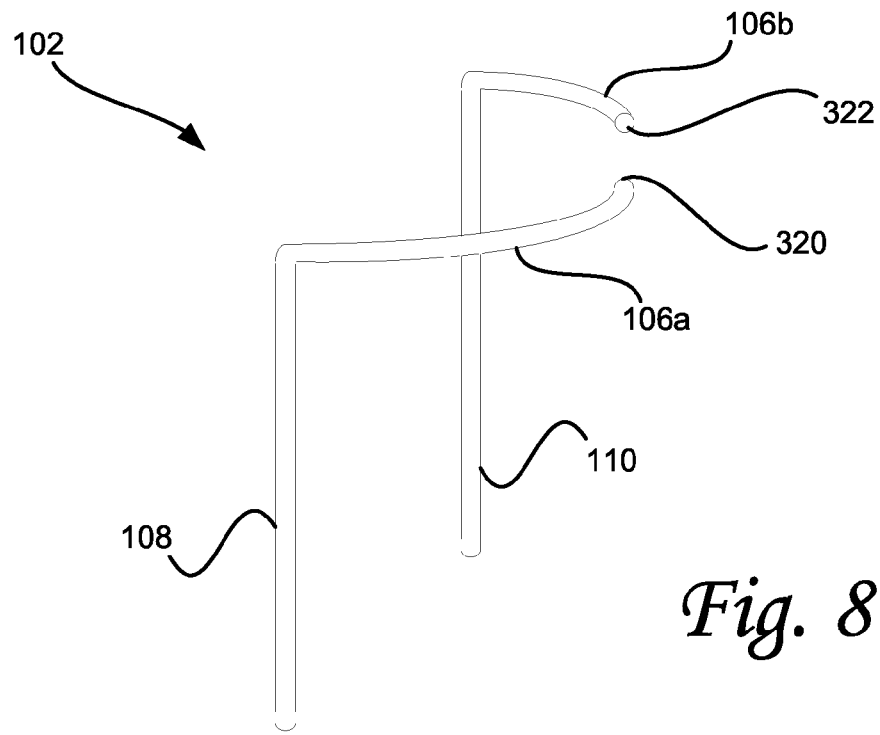
*Fig. 8*
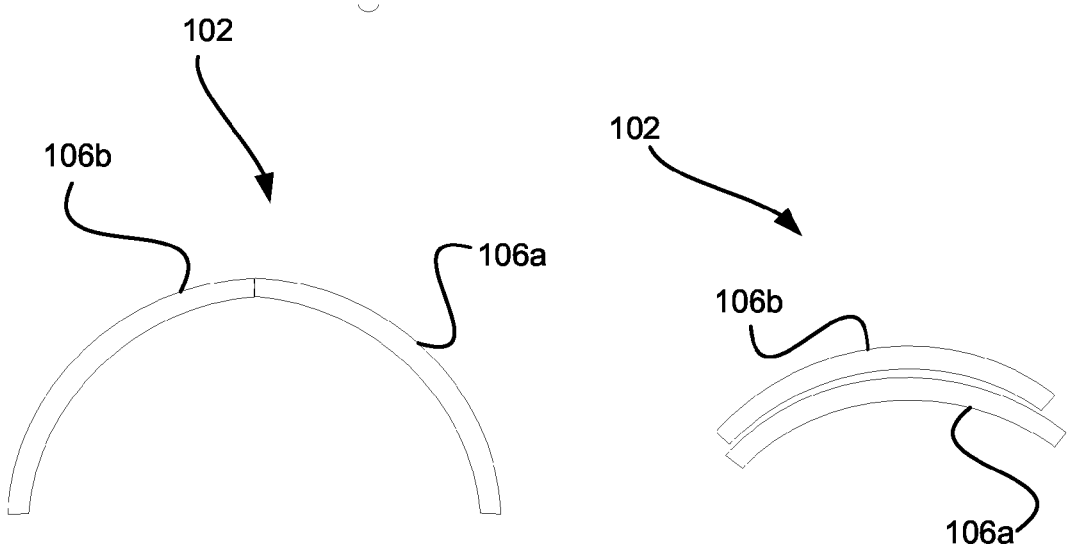
*Fig. 9a*   *Fig. 9b*

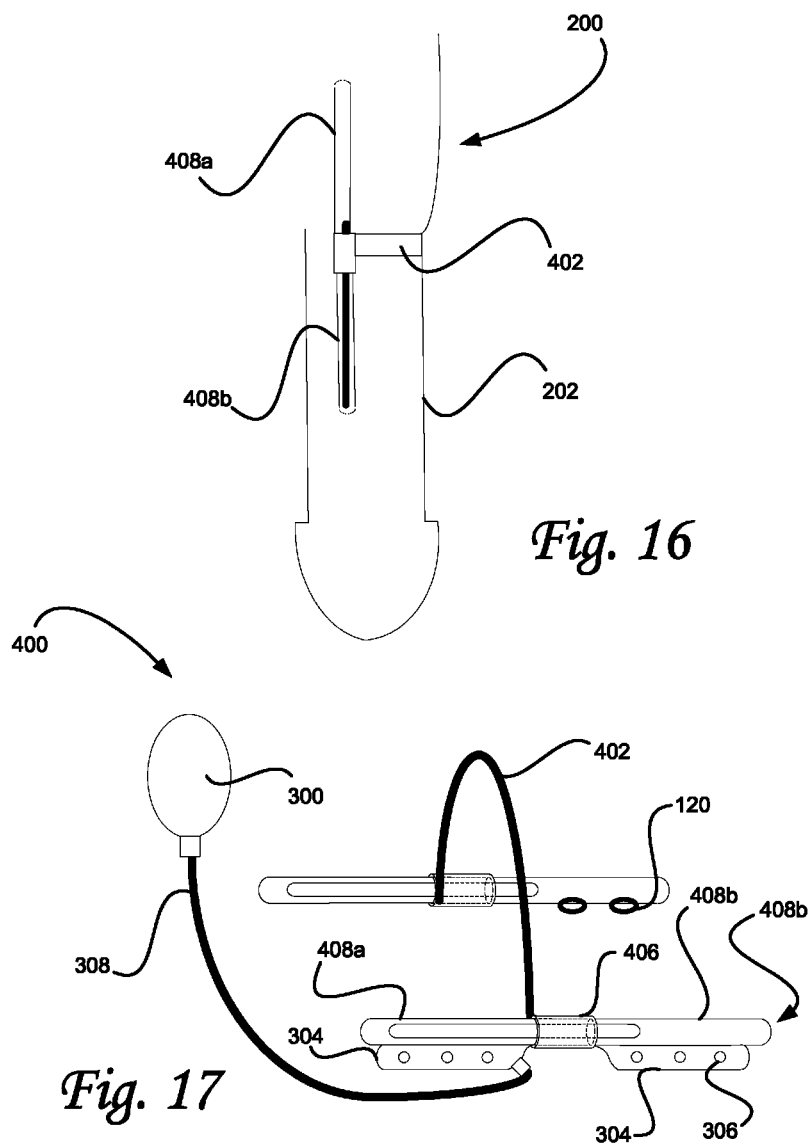

US 8,529,432 B1

PENILE IMPLANT FOR AIDING ACHIEVEMENT OF A PENILE ERECTION

TECHNICAL FIELD

The present invention, in some embodiments thereof, relates to the field of medical devices, and more specifically to medical devices for helping male subjects who experience erectile dysfunction achieve erection.

BACKGROUND OF THE INVENTION

Erectile dysfunction (ED) is sexual dysfunction characterized by the inability to develop or maintain firmness of the penis (an erection) during sexual performance.

A penile erection is the hydraulic effect of blood entering and being retained in sponge-like bodies within the penis. The process is often initiated as a result of sexual arousal, when signals are transmitted from the brain to nerves in the penis. Erectile dysfunction is indicated when an erection is difficult to produce. Endocrine, psychogenic, vascular, traumatic or iatrogenic origins are example of underlying causes of erectile dysfunction.

Erectile dysfunction is generally treated or managed via medication, external devices (e.g., penis pumps), or surgical implants. Surgical implants may be semi-rigid devices or inflatable devices. Semi-rigid devices range from permanently erect ones that cannot be altered to malleable ones that can be bent into position where appropriate. Some of the known implants consist of a pair of malleable rods surgically implanted within the erection chambers of the penis. With this type of implant the penis is always semi-rigid and merely needs to be lifted or adjusted into the desired position. Hydraulic, inflatable prosthesis also exist. These use fluid and are inflated or deflated on demand. Both inflatable and non-inflatable implants are implanted deep inside of penis corpus carvenosa.

BRIEF SUMMARY OF EMBODIMENTS OF THE INVENTION

Some semi-rigid devices generally keep the penis in a constant semi-rigid mode, even when erection is not required or desirable. Thus, semi-rigid devices may cause discomfort to the patient. Inflatable devices generally need to be filled with a fluid from an external source, in order to cause an erection. Moreover, the state-of-the-art implants (particularly the inflatable ones) are known to compress penile inner tissue and vasculature, resulting in atrophy and disfigurement of penis in significant proportion. Use of inflatable implants tends to diminish the likelihood of natural erection. Thus, a novel surgically implanted device is needed in the art.

The present invention aims to provide means assist a patient to maintain vaginal penetration during the course of intercourse and optionally to evoke natural erection, while incurring minimal surgical invasion to penis. A device of the present invention comprises at least two elongated rods which are configured for glide in and out penis shaft though lubricated sleeves implanted subcutaneously between deep and superficial penile fascia or just over the superficial fascia in each side. The rods are joined to an interconnecting structure which is joined to the rods to each other and stabilizes the rods within the penis shaft. When not deployed in the shaft, the rods may be retracted into the suprapubic or perineal region.

When moved into the penis shaft, the rods enable artificial erection and help preserve the firmness needed to perform and maintain vaginal penetration. In this manner, the patient can experience vaginal stimulation and obtain firm natural erection. The device of the present invention may also enable maintaining penetration after ejaculation. When maintaining the erection is no longer required, the rods are retracted from the penis shaft, enabling the penis to return to its flaccid state.

Because the rods are retractable, the device of the present invention enables attaining erection only when needed, without a need for external fluids to be inserted into the patient's body every time the device is to be used. Moreover, thanks to its size and structure, the device of the present invention causes minimal injury and invasion of penile tissue, and does not hinder the achievement of natural erection.

Thus, an aspect of some embodiments of the present invention relates to an implant for helping a male patient achieve a penile erection, the implant comprising a pair of substantially straight and substantially rigid rods and an interconnecting structure. The rods are configured for being implanted subcutaneously in the patient and are selectively movable from a retracted mode of the implant to a deployed mode of the implant. In the deployed mode the rods are within the penis shaft, while in the retracted mode at least a majority of each rod is out of the penis shaft. The interconnecting structure is implanted subcutaneously in the patient and joined to the rods, and is configured for stabilizing the rods within the penis shaft.

The interconnecting structure is may be configured for moving with the rods or for being substantially static.

In some embodiments of the present invention, device is provided for helping a male patient achieve a penile erection. The device comprises the above-described implant and a sealed, hollow, flexible sheath. The implant is in the form of a rod unit which comprises the rods and a substantially rigid curved section having a first and a second end, the curved section forming the interconnecting device and each rod being joined to a respective end of the curved section and extending away from the curved section at non-zero angle with a plane which includes the curved section. The rods extend away from the curved section in the same direction. The sheath is configured for enclosing the rod unit, and comprises a body portion, and two thin elongated legs extending away from one side the body portion. The body portion is configured for enclosing at least a majority of the rod unit when the rod unit is retracted within the body portion, and the legs are configured for enclosing the rods when the rod unit is deployed out of the body portion. The rod unit is selectively movable from a retracted mode thereof to a deployed mode thereof, where in the retracted mode at least a majority of the rod unit is within the sheath's body part, and in the deployed mode the rods are enclosed in the respective legs of the sheath.

Optionally, the body portion is configured for being subcutaneously implanted in the patient's pubic region above the patient's penis, and the legs are configured for being implanted along sides of a shaft of the patient's penis below a skin of the penis and above a deep or superficial fascia of the penis. The rod unit is selectively movable from the retracted mode thereof to the deployed mode thereof, where in the retracted mode the rod unit does not extend along the penis shaft, and in the deployed mode the curved section holds a base of the penis and stabilizes the rods while the rods are enclosed in the respective legs of the sheath and thus provide rigidity of the penis shaft.

In a variant, the non-zero angle between rods and the plane which includes the curved section is between about 60 degrees and 120 degrees.

In another variant, the curved section is somewhat flexible.

In yet another variant, the sheath comprises and encloses lubricant material.

In a further variant, the above device comprises at least one loop joined to an outer surface of at least one leg of the sheath.

In an additional variant, the curved section of the rod is configured for being located in a vicinity of a suspensory ligament of the penis, when the rod unit is in the deployed mode.

According to some embodiments of the present invention, the above device further comprises a hollow reservoir, a conduit, and perforated enclosure. The hollow reservoir is configured for being implanted in the patient's body, and for receiving and holding a fluid. The conduit has a first end in fluid communication with the hollow reservoir, and a second end. The perforated enclosure is joined to an outer surface of at least one leg and extends along a length of the at least one leg. The perforated enclosure is in fluid communication with the conduit's second end and has at least one opening configured for releasing the fluid delivered to the perforated enclosure from the reservoir via the conduit into the patient's body.

Optionally, the above device comprises a valve at a junction between the reservoir and the conduit, the valve being configured for enabling the fluid's flow from the reservoir to the conduit, when at least a predetermined pressure is exerted on the reservoir.

In a variant, the rod unit comprises two sections removably joinable to each other, the first section comprising a first portion of the curved section and a first one of the rods and the second section comprising a second portion of the curved section and a second one of the rods, such that the first portion of the curved section is removably joinable to the second portion of the curved section.

In another variant, the rod unit comprises plurality of rods substantially parallel to each other and joined to the curved section.

Optionally, the sheath comprises a plurality of legs, each leg being configured for enclosing a respective one of the rods.

According to some embodiments of the present invention, there is provided a device for being implanted in a body of the patient and for helping a male patient achieve a penile erection. The device includes the above-mentioned implant and two sealed flexible sleeves. The implant comprises the pair of rods, and the interconnecting structure comprises a curved base frame and two tubes. The curved base frame is substantially rigid and has two ends. Each tube is joined to the curved base frame near a respective end of the curved base frame, and extends away from the curved base frame, the tubes being at a non-zero angle with a plane which includes the curved base frame. Each tube is traversed by a respective one of the flexible sleeves. Each sleeve encloses a respective one of the rods. Each rod is selectively movable within the respective sleeve between a rear side of the curved base frame and a front side of the curved base frame.

Optionally, the curved base frame is configured for being implanted in a pubic region in a vicinity of a base of a penis of the patient, to encircle a portion a base of a penis of the patient, and for being implanted below a skin of the penis and above or within or below a suspensory ligament of the penis. Each tube is implanted below the skin in a vicinity of the penis base. The first portion of each sleeve on the rear side of the curved base frame is configured for being implanted along a root of the penis or below a skin on a pubic area of the patient. The second portion of each sleeve on the front side of the curved base frame is configured for being implanted along a shaft of the patient's penis. Each rod is selectively movable within the sleeve between the rear side of the curved base frame and the front side of the curved base frame, such that the rods provide rigidity to the penis shaft when located in the second portions of the respective sleeves.

In a variant, the curved base frame is somewhat flexible.

In another variant, at least one of the sleeves comprises and encloses lubricant material.

In yet another variant, the device includes at least one loop joined to an outer surface of at least sleeve on the front side of the curved base frame.

In a further variant, the device further comprises a hollow reservoir, a conduit, and a perforated enclosure. The hollow reservoir is configured for being implanted in the patient's body and for receiving and holding a fluid. The conduit has a first end in fluid communication with the hollow reservoir, and a second end. The perforated enclosure is joined to an outer surface of at least one sleeve and extending along at least part of a length of the at least one sleeve, the perforated enclosure being in fluid communication with the conduit's second end and having at least one opening configured for releasing the fluid delivered to the perforated enclosure from the reservoir via the conduit into the patient's body.

Optionally, the device comprises a valve at a junction between the reservoir and the conduit, the valve being configured for enabling the fluid's flow from the reservoir to the conduit, when at least a predetermined pressure is exerted on the reservoir.

In a variant, the device comprises: a plurality of tubes joined to the curved base frame; a plurality of sleeves, each traversing a respective tube; and a plurality of rod, each enclosed within a respective sleeve.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

FIGS. 8, 9a and 9b are a drawings illustrating an embodiment of the present invention in which the rod unit includes two sections which are removably joinable to each other;

FIGS. 15 and 16 illustrate a use of the device of FIG. 11, in which one side of the sleeve is implanted in the pubic region while another side of the sleeve is implanted in the shaft of the penis;

FIG. 17 is a schematic drawing illustrating an embodiment of the present invention, in which the device of FIG. 11 includes a perforated enclosure joined to an outer surface of the portion of the sleeve implanted in the penis shaft and/or a plurality of loops joined to an outer surface of the portion of the sleeve implanted in the penis shaft.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

Figures 1A, 1B:
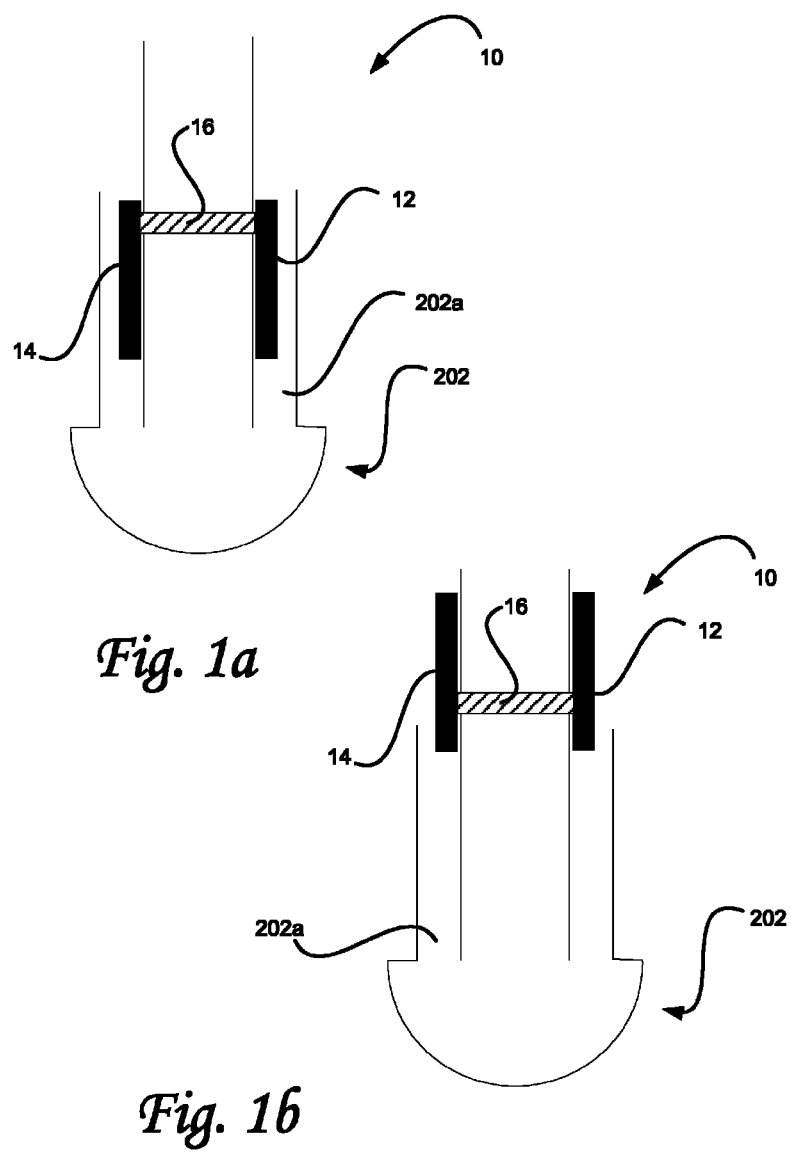
FIGS. 1a and 1b are schematic drawings illustrating a device of the present invention, in its deployed mode and retracted mode.

Referring now to the drawings, FIGS. 1a and 1b are schematic drawings illustrating a device 10 of the present invention, in its deployed mode (FIG. 1a) and retracted mode (FIG. 1b).

The device 10 of the present invention includes a first rod 12, a second rod 14, and an interconnecting structure 16. The rods 12 and 14 and the interconnecting structure 16 are configured for being implanted subcutaneously in a patient. In the device's deployed mode, the rods 12 and 14 are located in the penis shaft 202 under the skin 202a and provide rigidity to the penis during sexual intercourse. In the device's retracted mode, the rods 12 and 14 are retracted away from the penis shaft, and allow the penis to return to its flaccid state. When not deployed in the shaft, the rods may be retracted into the suprapubic or perineal region.

The interconnecting structure 16 is joined to the rods and stabilizes the rods within the penis shaft. The interconnecting structure may move with the rods, or may be substantially static while the rods move into and away from the penis shaft.

FIGS. 2 to 10 exemplify some embodiments of the present invention in which the interconnecting structure moves with the rods. FIGS. 11 to 18 exemplify some embodiments of the present invention in which the interconnecting structure substantially does not move with the rods.

Figure 2:
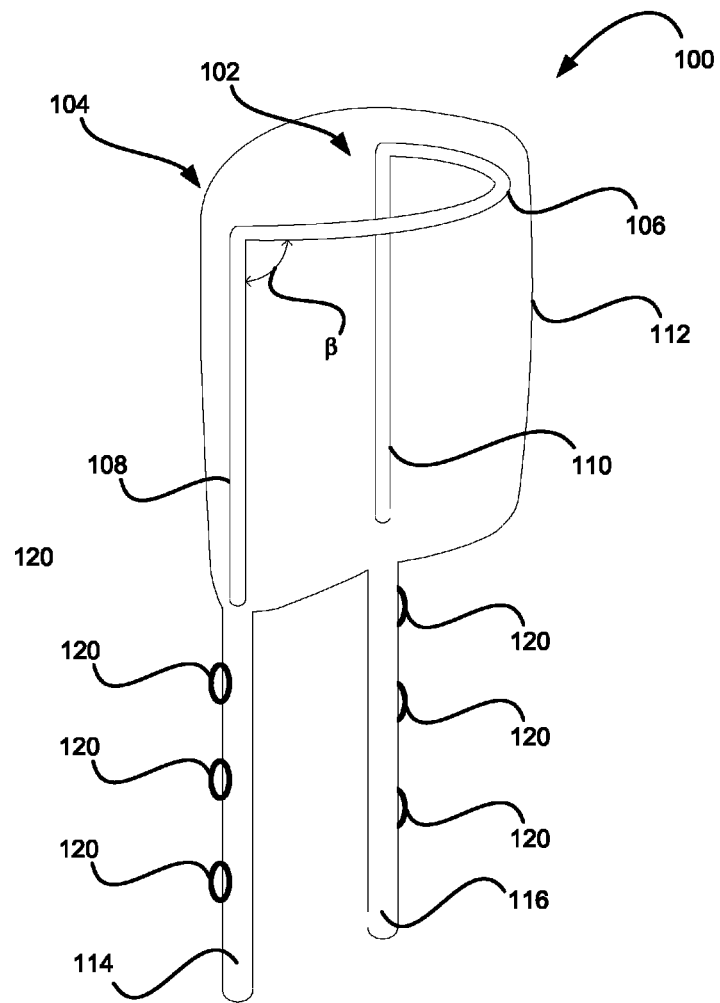
FIGS. 2 and 3 are schematic drawings illustrating an embodiment of the present invention, in which the device of the present invention includes a rod unit which may be movable within a sheath.
Figure 3:
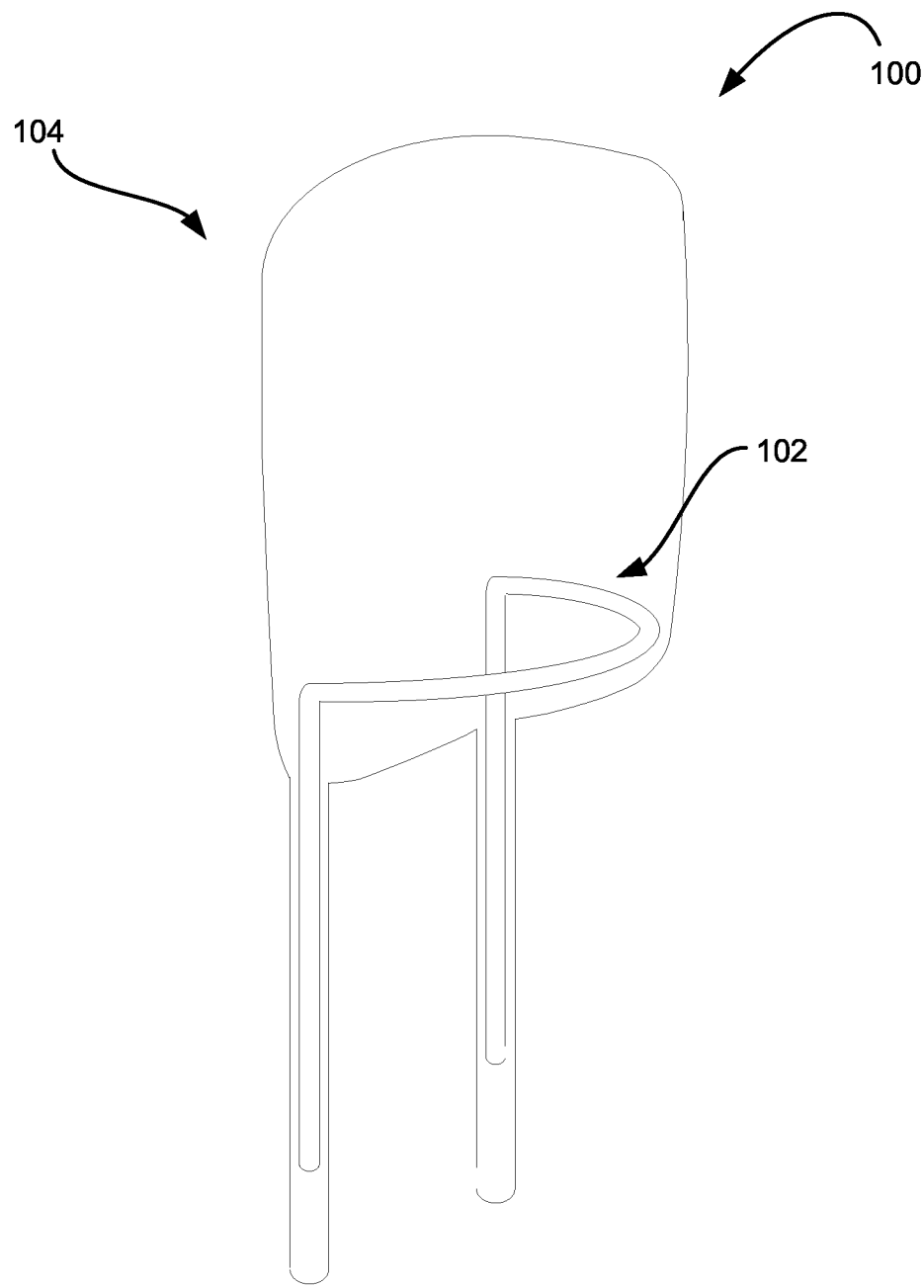

Referring now to FIGS. 2 and 3, schematic drawings illustrate an embodiment of the present invention, in which a device 100 of the present invention includes a rod unit 102 which may be movable within a sheath 104. The device 100 is configured for being surgically implanted into a patient's body, and is configured to be manipulated by the patient, in order for the patient to achieve an erection.

The rod unit 102 includes a curved section 106 and two substantially straight rods 108 and 110. The rod unit 102 is an example of the device 10 of FIGS. 1a and 1b. The rods 108 and 110 correspond to the rods 10 and 12 of the device 10, whiles the curved section 106 is an example of interconnecting structure 16 of the device 10.

The curved section has two ends and is therefore not a loop. The rods 108 and 110 are joined to respective ends of the curved section 106. The rods 108 and 110 extend away from the curved section 106 and are at non-zero an angle β with a plane which includes the curved section 106. The rods 108 and 110 extend away from the curved section 106 in the same direction. In some embodiments of the present invention, the angle β is between 60° and 120°. The curved section 106 has an open shape, as it is designed to surround a section of the base of the penis which does not include the ventral section on the penis's base. The curved section 106 may be shaped like a portion of a circle, for example like a semicircle.

The rod unit 102 may be cast as a single unit, or may be made of different units joined to each other by a locking mechanism (screw, adhesive, press-fit, etc.). The presence of the curved section and its linking to the rods limit the motion of the rods with respect to each other. Thus the curved section stabilizes the position and orientation of the rods with respect to each other and the penis. The rods are substantially rigid, as they are meant to impart rigidity to the penis to enable the penis to sustain vaginal penetration, when the rods are located along sides of the penis's shaft. Optionally, curved section 106 is rigid, yet flexible. This enables a user (patient) to bend the curved section 106, in order to adjust the strength of the hold of the curved section 106 onto the base of the penis. The strength of the curved section's hold on the base of the penis may be increased by pushing the curved section inwards and thus tightening the curve. The strength of the curved section's hold on the base of the penis may be decreased by pulling the ends of the curved section outwards and thus stretching the curve. The latter may be performed in order to accommodate and penis that is enlarged during erection.

In a variant, the curved section 106 and the rods 108 and 110 are made of substantially rigid or copper with or without some tensile quality. In another variant, the curved section 106 and the rods 108 and 110 are made of a polymer plastic material. Rigid or semi-rigid flexible plastic material produced by mold extrusion, may be a fitting example, since this kind of plastic material can be manufactured to be durable and biocompatible. In yet another variant, the curved section 106 and the rods 108 and 110 are made of plastic-encased copper.

The sheath 104 is a hollow, closed (sealed) element configured for enclosing the rod unit 102. The sheath 104 includes body portion 112 and two thin elongated legs 114 and 116 extending away from one side of the body portion. The sheath 104 is configured for being implanted subcutaneously in the patient's genital region, such that the body portion 112 is in the pubic region and legs 114 and 116 extend along each side of penis shaft underneath the skin. The legs 114 and 116 may be implanted either between the deep fascia and the superficial fascia, or above the superficial fascia and under the skin. The sheath 104 is flexible (elastic) and soft, while being durable. The body portion 112 is configured for being implanted in the pubic region of the patient, above the patient's penis. The body portion 112 is large enough to contain at least a majority of the rod unit, when the rod unit 102 is retracted in the pubic region (see FIG. 2). The legs 114 and 116 extend away from the rod unit, are configured for being implanted along sides of the penis' shaft. The legs 114 and 116 and are configured for receiving rods 108 and 110, respectively, when the rod unit 102 is deployed to the penis shaft to provide rigidity to the penis (see FIG. 3). In a variant, the sheath 104 is made of membranous silicon. Optionally, the membranous silicon or any other material forming the sheath is thicker in body part than in legs, so that the sheath is somewhat rigid (e.g. rubbery) while the legs are membranous and thin.

Optionally, the sheath 104 is at least partially filled with a lubricant (e.g. a biocompatible lubricant), to ease the movement of the rod unit 102 within the sheath 104. In a variant, the device 100 includes a plurality of loops 120 joined to an outer surface of at least one leg of the sheath 104. The loops 120 may be used to ease suturing the sheath to an internal tissue of the patient, such as fascia or ligament, for example. The suture may be needed in order to prevent undesirable displacement of the sheath.

In a non-limiting example, the rod unit 102 may be configured as follows: a diameter of the rods and of the wire defining the curved section is about ⅛ to ¼ inches; a length of each rod is about 4-5 inches; a width of the curved section (i.e. the distance between the two rods) is about 1.5 to 2 inches; a depth of curved section (i.e., the maximal size along an axis perpendicular to the width of the curved section) is about 2 inches. It should be noted that the dimensions of the rod unit may vary according to the patient's individual need, as determined by a physician. Moreover, the physician may be able manufacture a rod unit 102 of desired dimensions, if stocks of the curved section 106 and rods 108 and 110, as well as tools to join the rods to the curved section are supplied.

Figure 4:
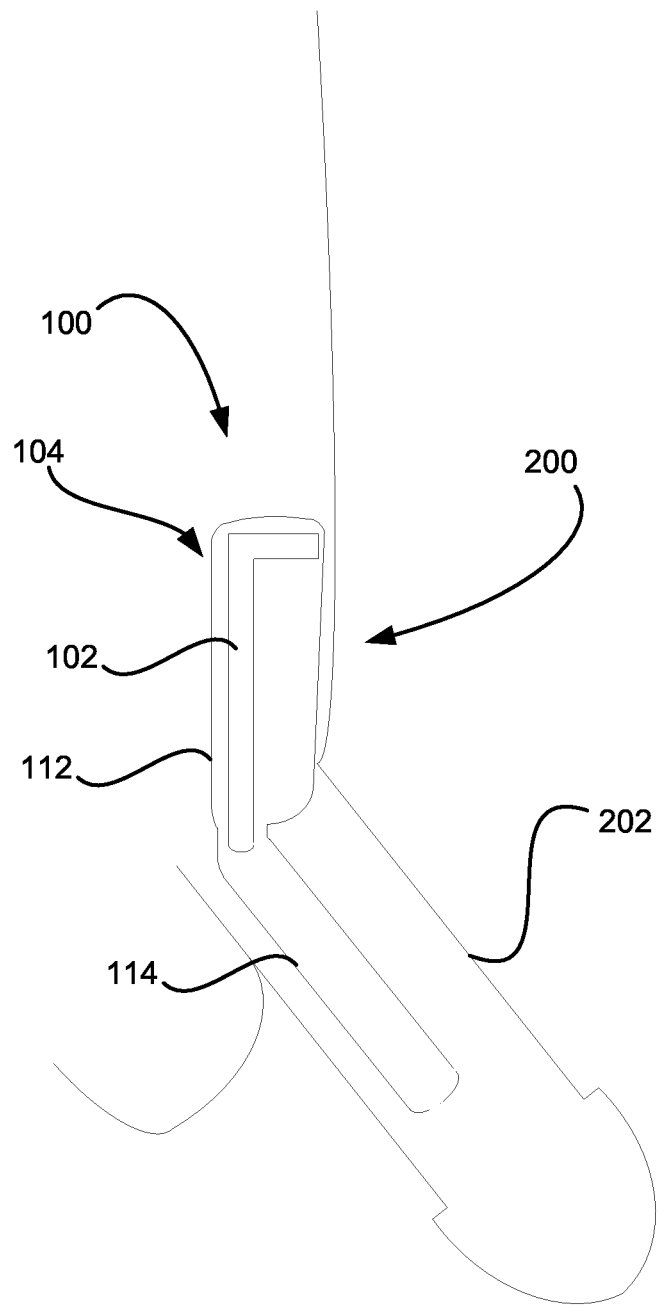
FIGS. 4, 5a, and 5b are schematic drawings illustrating the use of the device of FIGS. 2 and 3 when implanted within a patient.
Figure 5:
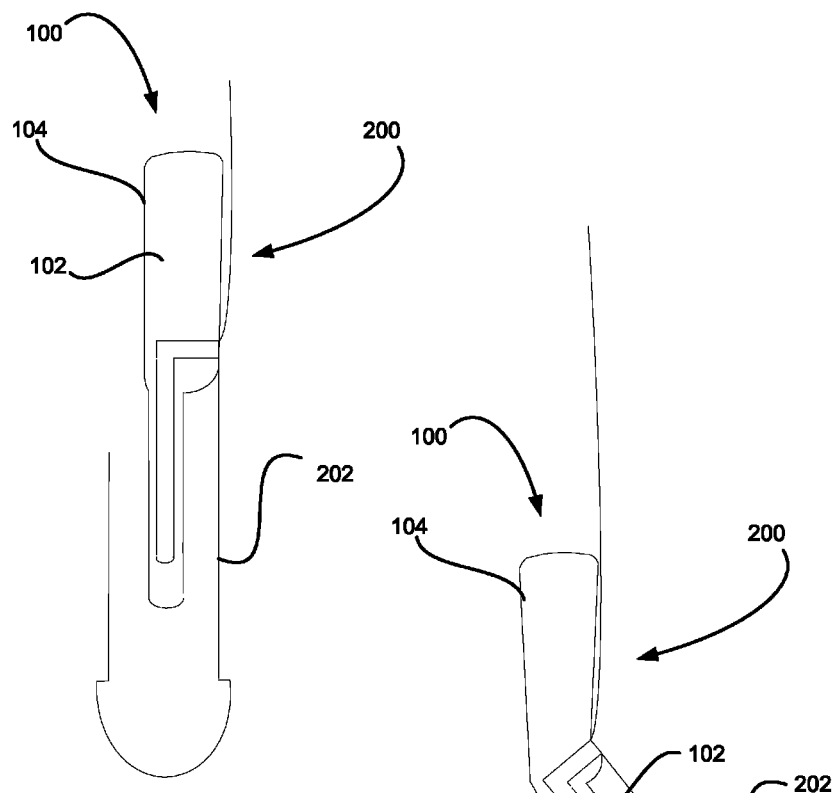

Reference in now made to FIGS. 4, 5a-5b, which are schematic drawings illustrating the use of the device of FIGS. 2 and 3 when implanted within a patient. In FIG. 4, the rod unit 102 is retracted within the body portion of the sheath 104. In FIG. 5a, the penis is rotated to deploy the rod unit into the legs of the sheath 104, in order to lend some rigidity to the penis. In FIG. 5b, the penis is released while the rod unit is deployed.

As mentioned above, the body section 112 of the sheath 104 is implanted below the skin of the pubic region 200, while the legs (of which only the leg 114 is shown) are implanted to extend along the shaft 202 of the penis. When the device 100 is not in use, the rod unit 102 is retracted within the sheath's body section in the pubic region (see FIG. 3). With the body section 112, the rods of the rod unit 102 are substantially vertical. Because under normal circumstances the penis is not vertical, the legs of the sheath are at an angle with the rods of the rod unit. This prevents the rod unit 102 to slide within the legs of the sheath.

When the patient wants to achieve an erection, he rotates or bends the penis shaft 202, so that the penis shaft assumes a vertical orientation (see FIG. 5a), enabling deployment of the rod unit 102. Following the penis' rotation, the legs of the sheath 104 extend vertically, and are aligned with the rods of the rod unit 102. Thus, the rod unit 102 slips downward and the rods of the rod unit 102 are held by the legs of the sheath 104. The curved section of the rod unit surrounds a portion on the base of the penis (except for the ventral section).

In FIG. 5b, the penis is released and returns to its natural orientation, while the rod unit is still in the deployed mode. It can be seen that the rod unit 102 is no longer vertical and is thus prevented from slipping back into the sheath's body section.

After completion of the sexual intercourse, the rod unit 102 may be guided back to the body section of the sheath 104. For this purpose, the penis is to be rotated or bent to assume vertical orientation, the rods of the rod unit are pushed up, until the rod unit is back within the body section of the sheath 104. The penis is then released to and returns to its natural orientation.

It should be noted that because the device is implanted in the soft tissue underneath the skin, the patient can easily handle the rod unit from outside: for example, the patient may push the rods upwards in order to cause the rod unit to retract, the patient may press on both ends of the curved section to strengthen the curved section's hold on the penis, and the patient may pull the ends of the curved section to weaken the curved section's hold on the penis.

Figure 6:
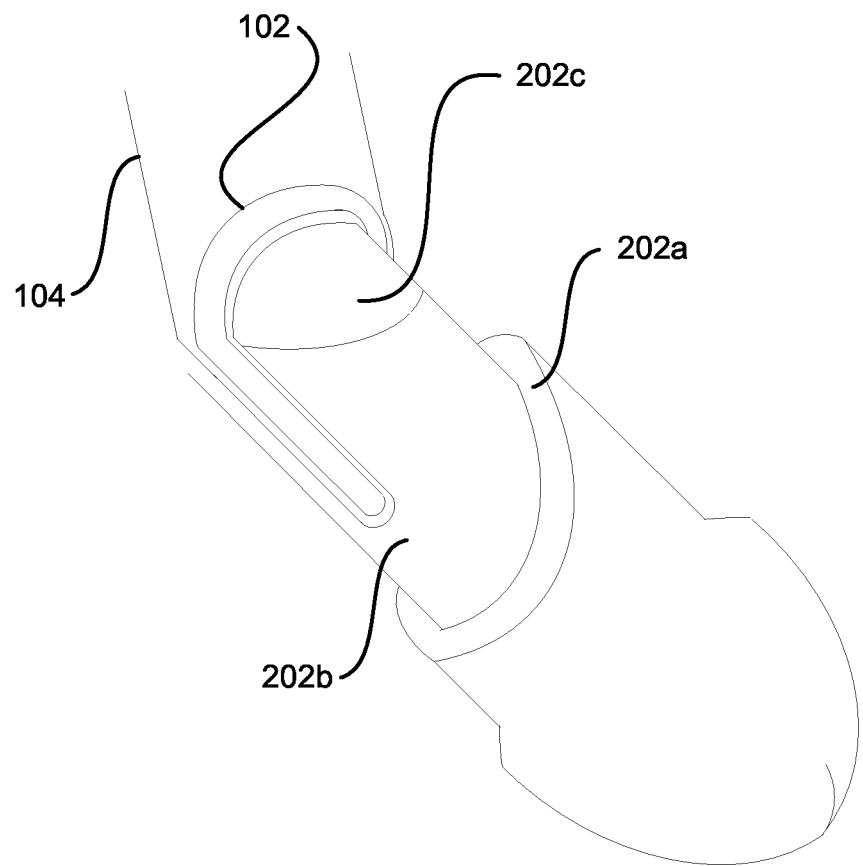
FIG. 6 is a perspective drawing illustrating a cutout of a penis in which the device of FIGS. 2 and 3 is implanted.

Reference in now made to FIG. 6, which is a perspective drawing illustrating a cutout of a penis in which the device of FIGS. 1 and 2 is engaged to provide rigidity to the penis.

As mentioned above, the device 100 is configured for being implanted under the patient's skin. In the penis shaft, the legs of the sheath 104 are under the patient's skin 202a and above the fascia 202b. As mentioned above, the fascia 202b may be the superficial fascia or the deep fascia. Thus, when the rod unit is deployed, the curved section of the rod unit 102 slides in the region of the suspensory ligament 202c at the base of the penis. Optionally, the curved section of the rod unit 102 holds the suspensory ligament 202c at the base of the penis.

Figure 7:
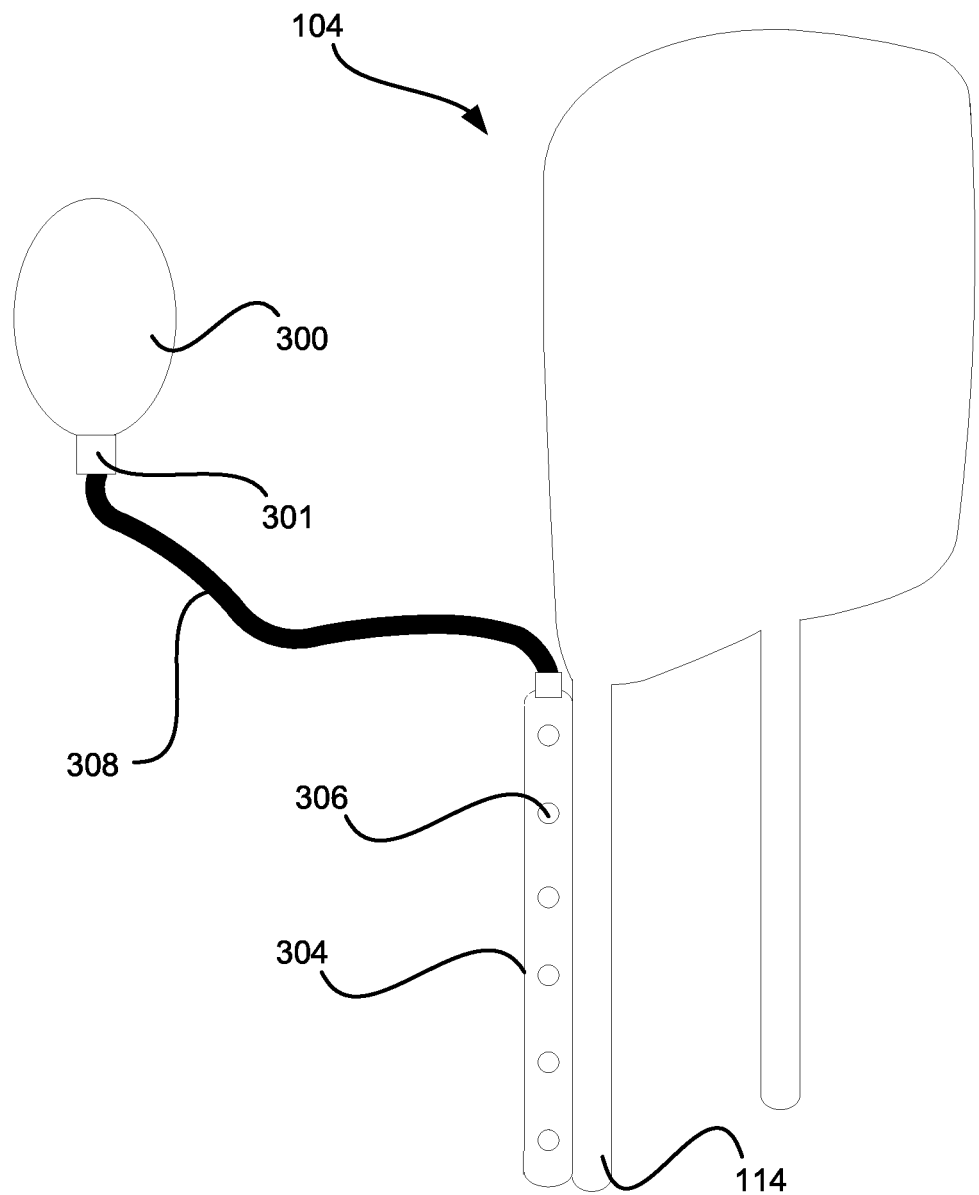
FIG. 7 is a schematic drawing illustrating an embodiment of the present invention in which a perforated enclosure is joined to an outer surface of at least one of the legs of the sheath.

Reference in now made to FIG. 7, which is a schematic drawing illustrating an embodiment of the present invention in which a perforated enclosure is joined to an outer surface of at least one of the legs of the sheath.

According to some embodiments of the present invention, the device 100 includes a perforated enclosure 304 joined to an outer surface of at least one leg of the sheath 104, and extending along the length of the leg. The perforated enclosure 304 has one or more openings 306. The perforated enclosure is in fluid communication with a hollow reservoir 300 via a conduit 302. Optionally, the reservoir 300 is implanted remotely in the patient's body, for example in lower abdominal area preferably.

The hollow reservoir 300 is configured for to receiving a fluid (e.g. a reagent and/or drug) from outside the patient's body (for example via an injection), and has an outlet 301 connected to conduit 308 for transferring the fluid to the perforated enclosure 304 via the conduit 308. In this manner, the fluid can be released into the patient's body through the openings 306, according to the patient's need. Preferably, the reservoir 300 includes a check valve at the outlet 301. The valve is configured for letting the fluid flow from the reservoir 300 to the conduit 308 when at least a predetermined pressure is exerted on the reservoir 300 (e.g., by a user pressing on the reservoir 300). The reservoir 300 may be made of resilient rubbery material, so as to be substantially self-sealing when punctured to receive the fluid.

The fluid contained within/injected to the reservoir 300 may, for example, include one or more of the following: a biological lubricant for reducing the skin's resistance to the movement of the rods, an anesthetic agent to reduce pain, an antibiotic to locally control infection, phentolamine to reduce ischemic tissue damage, a locally-acting biopharmalogical agent to help with erection or repair anatomical defect, and stem cells, neurotrophine etc if medically appropriate.

Optionally, live tissue may be wrapped around the sheath's legs along penis shaft. The live tissue blocks the direct contact of penile tissue with non-biological synthetic material of legs (even if this material is biocompatible), and thus minimizes the possibility of the penile tissue's reaction to a foreign body. Live tissue wrapped around the legs increases the volume of the legs any may thus help keep the implant firm and stable, since a larger legs may have an increased resistance to motion. The live tissue may include peritoneum and/or tissue from the user's genital region.

Reference in now made to FIGS. 8, 9a and 9b, which are drawings illustrating an embodiment of the present invention in which the rod unit 102 includes two sections which are removably joinable to each other. FIG. 8 is a perspective view of the rod unit 102. FIGS. 9a and 9b are top views of the rod unit 102 in its open mode and closed mode, respectively.

In this embodiment, the curved section 106 is formed by a first portion 106a having a first end 320 and a second portion 106b having a second end 322. The locking mechanism between the first portion 106a and the second portion 106b may be formed by a male member at the first end 320 and female member located at the second end 322.

When the rod unit 102 is stored in the sheath's body portion, the two sections may be separated and the first portion 106a and second portion 106a are slid one over the other (see FIG. 9b). In this manner, the space required to store the rod unit in the sheath's body is reduced. When the rod unit is deployed in the sheath's legs, the two sections may be rejoined to each other.

Figure 10:
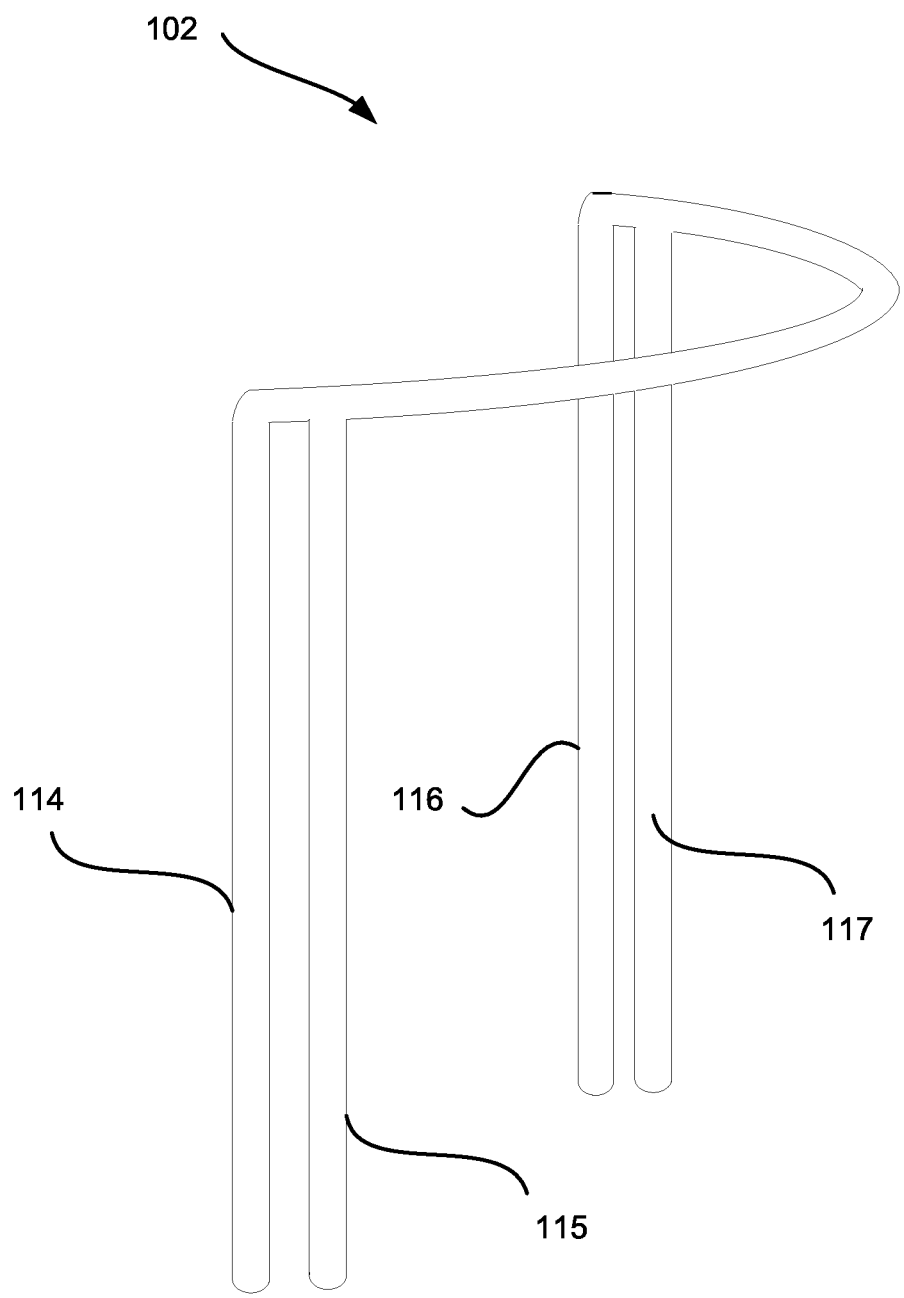
FIG. 10 is a perspective drawing illustrating an embodiment of the present invention in which the rod unit includes a plurality of rods.

Reference in now made to FIG. 10, which is a perspective drawing illustrating an embodiment of the present invention in which the rod unit includes a plurality of rods.

So far, the device 100 has been described having two rods in the rod device and two legs in the sheath. The present invention is not limited to this case. If fact, the rod device may include any number of substantially parallel rods (two, three, four, or more) joined to the curved section, and the sheath may include a corresponding number of legs, each leg being configured for accommodating a respective rod. By way of example, FIG. 10 illustrates a rod unit 102 having four rods 114, 115, 116, and 117.

Figure 11:
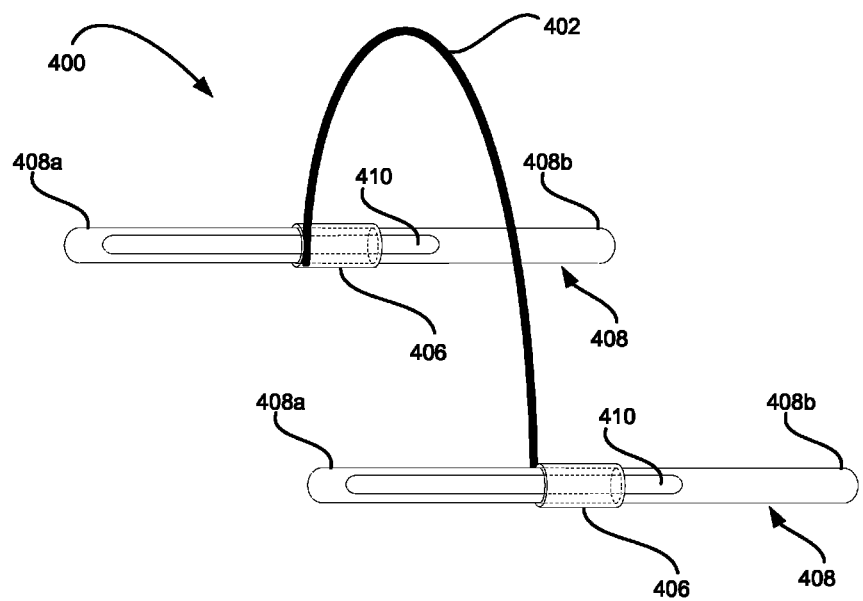
FIG. 11 is a perspective drawing illustrating a device of the present invention which includes a curved base frame joined to at least two hollow tubes in the vicinity of the curved base frame's ends, each tube holding a sealed sleeve enclosing a rod which can be moved within the sleeve.
Figure 12:
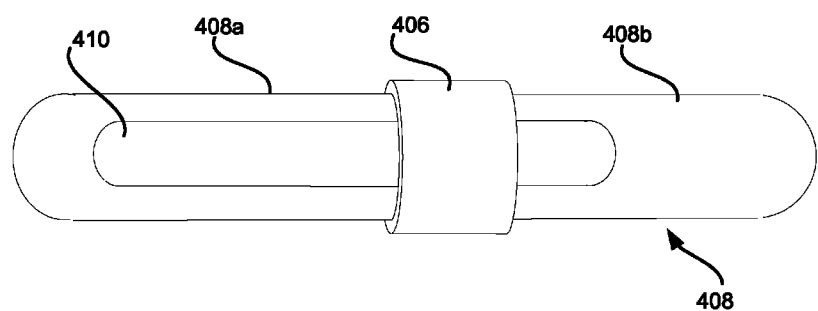
FIG. 12 is a detail drawing of an assembly formed by a tube, a sleeve, and rod in the device of FIG. 11.

Reference in now made to FIGS. 11 and 12, which are perspective drawings illustrating a device 400 of the present invention which includes a curved base frame 402 joined to two hollow tubes 406, each tube holding a sealed sleeve 408 enclosing a rod 410 which can be moved within the respective sleeve through the aperture of the base. The device 400 is an example of the device 10 of FIGS. 1a and 1b. The rods 410 correspond to the rods 10 and 12 of the device 10, while the assembly formed by the curved base frame 402 and the tubes 406 is an example of interconnecting structure 16 of the device 10.

FIG. 11 shows an example of the device 400, in which the curved base frame 402 is a curved wire having two ends, each end being joined to a respective hollow tube. FIG. 12 is a blown-up drawing illustrating the arrangements of a tube, a sleeve, and a rod.

The device 400 includes a curved base frame 402, at least two tubes 406, at least two sealed sleeves 408, and at least two rods 410. The curved base frame 402 is configured for being surgically implanted at the base of a patient's penis, below the skin and above or within or below the suspensory ligament, while not invading to penile fascia. When implanted, the curved base frame 402 is configured for being located in the pubic region in the vicinity of the base of the penis, to encircle a portion of the penis, while leaving the ventral section of the penis free. The curved base frame is substantially rigid, but may be somewhat flexible, in order to enable the patient to control the strength by which the curved base frame holds the penis via the rods. The curved base frame may be made of semi-rigid and/or semi-flexible metal and/or plastic materials.

The curved base frame has two ends. Two hollow tubes 406 are joined to the curved base frame in the vicinity of the respective ends of the curved base frame 402. Each tube 406 extends away from the curved base frame, and is at an angle with a plane which includes the curved base frame. The tubes may be perpendicular to the plane of the curved base frame. When the device 400 is implanted in the penis, each tube 406 is located near or at the base of the penis, and extends toward the shaft of the penis. The tube 406 is traversed by a sealed sleeve 408 having a first portion 408a and a second portion 408b. The first portion 408a is on a first (rear) side of the base 402 and extends away from the penis shaft, along the penis root or in the pubic region. The second portion 408b is on a second (front) side of the base 402 and is configured for being implanted to extend along the penis shaft. The sleeve is flexible (elastic) and soft, while being durable. Each sleeve 408 encloses a respective rigid rod. The rod is movable within the sleeve.

Optionally, the sleeves and rods are implanted before the curved base frame and tubes. The sleeves may be implanted either from perineal region (penis root) or from lower abdominal pubic region to the penis shaft. If the sleeves are preimplanted, the sleeves are to be inserted inside the respective tubes before implanation is completed. For this purpose, each tube may be somewhat elastic and may have a slit. In this manner, the each sleeve may be inserted in the corresponding tube via the slit, while requiring a minimal external force to force the tube open for insertion. The elasticity of the tubes will cause the tubes the close after the insertion of the sleeves is completed.

In a preferred embodiment of the present invention, each tube is a rigid member having dimensions selected for allowing the respective rod to move along the tube's central axis, while limiting the movement of the respective rod in other directions. Thus, the assembly formed by the curved base frame 402 and the tubes 406 (the interconnecting structure) stabilizes the rods when the rods are in the penis shaft, by limiting changes in position and orientation of the rods.

Optionally, a diameter of the second portion 408b of the sleeve is larger than the diameter of the sleeve's first portion 408a, so that circumferential pressure exerted on the rod by the second portion 408b is lower than the circumferential pressure exerted on the rod by the first portion 408a. In this manner, the rod is less likely to retract from sleeve's first portion 408a into the second portion 408b.

The sleeve 408 may contain a lubricant to ease the rod's movement between the first portion and the second portion of the sleeve.

According to a non-limiting example, a length of the rod 410 may be about 4 to 5 inches, and a length of the tube 406 may be about 0.5 to 1 inches. The diameter of the rod is about ¼ to ⅛ of an inch. The dimensions of the curved base frame may be similar to the dimensions of the curved section of FIGS. 2 to 10.

In some embodiments of the present invention, the portion of the device 400 formed by the curved base frame 402 and the tubes 406 may be made of a single piece of material and manufactured via injection mold.

Figure 13:
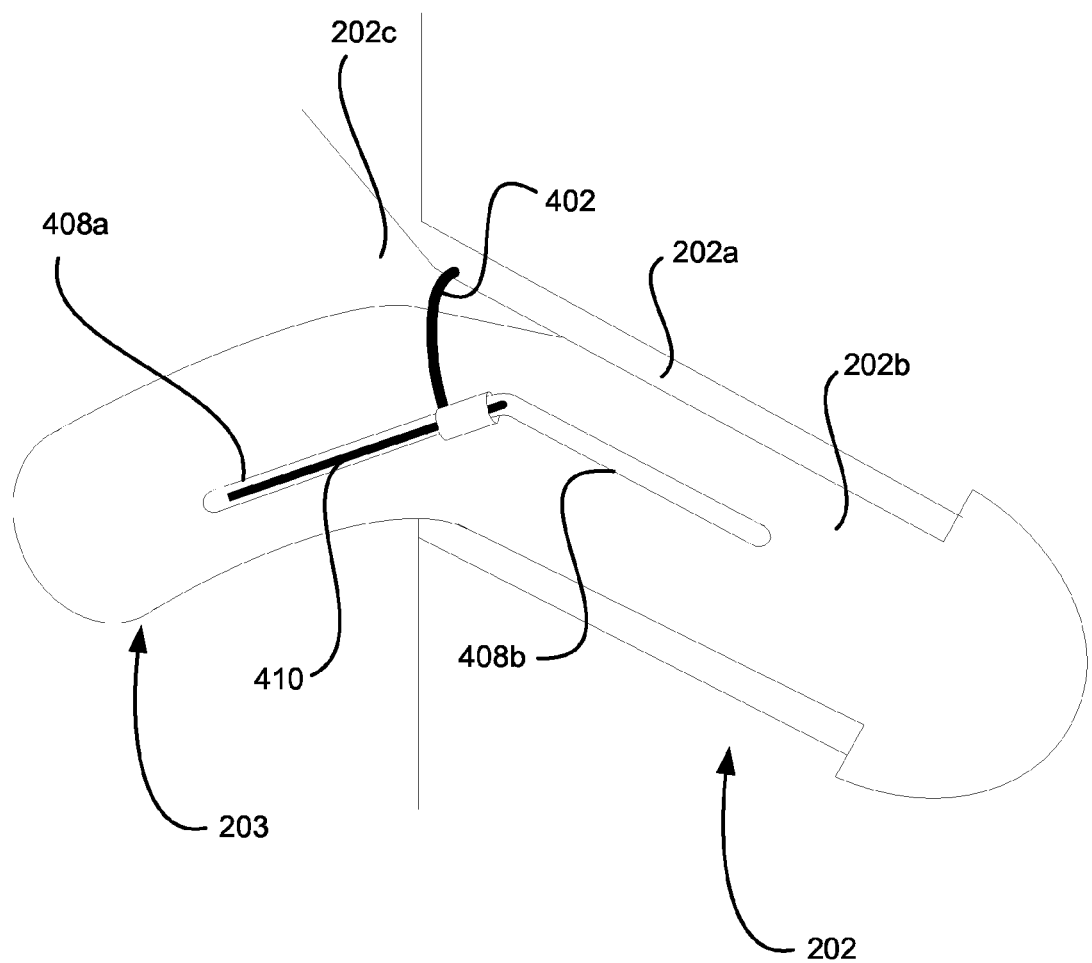
FIGS. 13 and 14 illustrate a use of the device of FIG. 11, in which one side of the sleeve is implanted in the root section of the penis while another side of the sleeve is implanted in the shaft of the penis.
Figure 14:
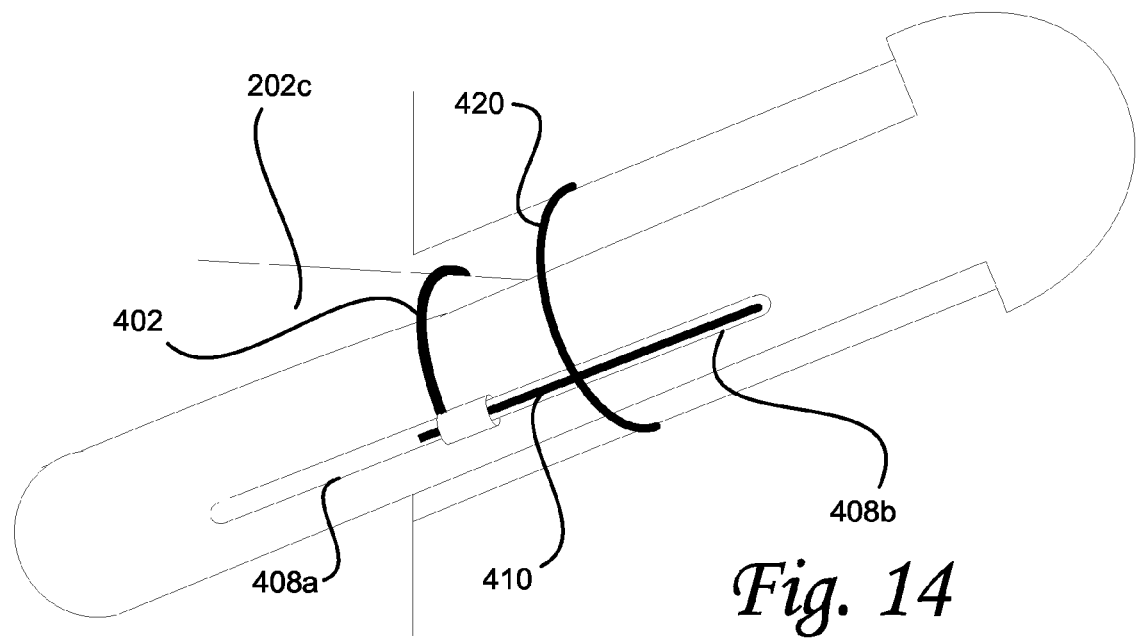

Reference in now made to FIGS. 13 and 14, which illustrate a use of the device of FIG. 11, in which one side of each sleeve is implanted in the root section of the penis while another side of the sleeve is implanted in the shaft of the penis. In FIG. 13, each rod is retracted in the root section of the penis. In FIG. 14, each rod is deployed in the shaft of the penis, to increase the rigidity of the shaft of the penis.

In the example of FIGS. 13 and 14, the base 402 holds the base of the penis, below the skin 202a and above or within or below the suspensory ligament 202c, without exposing the fascia 202b. The first portion 408a of the sleeve is implanted to extend along the root 203 of the penis. The second portion 408b of the sleeve is implanted in the penis shaft, below the skin 202a and above the fascia 202b. As mentioned above, the fascia 202b may be the superficial fascia or the deep fascia.

When an erection is not needed, each rod is retracted in the first portion 408a of the sleeve (FIG. 13). When an erection is not needed, the rod does not slide from the first portion 408a to the second portion 408b of the sleeve, since the first portion is at a non-zero angle with the second portion.

In order to deploy the rod 410 to the penis shaft, the penis is rotated so that the second portion 408b is aligned with the first portion 408a of the sleeve (FIG. 14). The user pulls the rod 410 to the second portion 408b of the sleeve. Then, the penis is released, so that the first portion 408a and the second portion 408b of the sleeve are again at an angle. Thus, when the rod is deployed in the penis shaft, the rod may not freely slip into the first portion 408a, because of the non-zero angle between the first and second portion.

Optionally, a ring 420 may be placed on the exterior of the penis shaft to apply pressure on the rods, in order to ensure that the rods do not slide back into the first portion 408a during sexual intercourse. In a variant the ring 420 has elastic properties, so that it constricts the penis when placed upon the penis.

Figure 15:
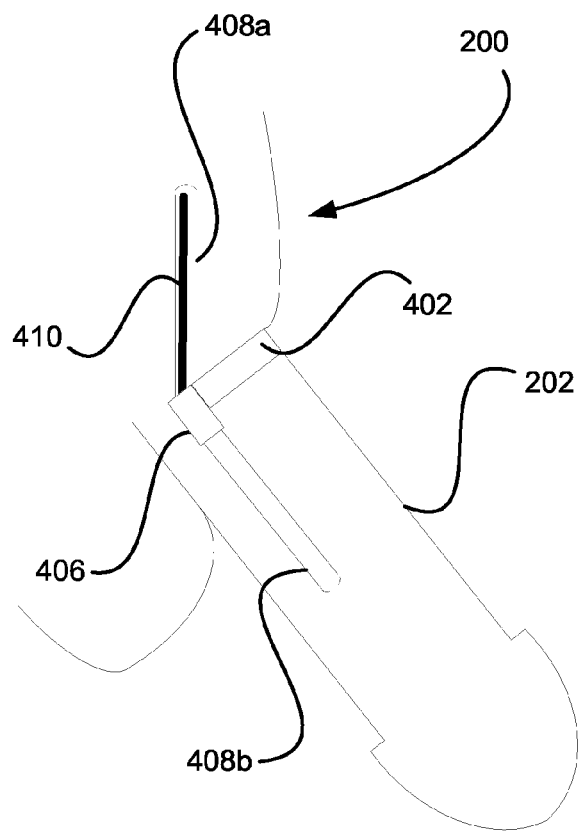

Reference in now made to FIGS. 15 and 16, which illustrate a use of the device of FIG. 11, in which one side of the sleeve is implanted in the pubic and low abdominal region while another side of the sleeve is implanted in the shaft of the penis. In FIG. 15, each rod is retracted in the pubic abdominal region. In FIG. 16, each rod is deployed in the shaft of the penis, to increase the rigidity of the shaft of the penis.

The arrangement of FIGS. 15 and 16 is similar to that of FIGS. 13 and 14. The only difference lies in the fact that in FIGS. 15 and 16, the first portion 408a of the sleeve is implanted in the pubic and low abdominal region and extends substantially vertically. The penis' natural orientation is not vertical, thus when the penis is in its natural orientation, the rod 410 may not slide between the first and second portions of the sleeve. This helps maintain the rod retracted or deployed, as needed.

In order to deploy the rod to the penis shaft, the penis is rotated to assume a vertical orientation. In this manner the second portion 408b is aligned with the first portion 408a, and the rod 410 slips through the tube to the second portion 408b. In order to retract the rod back into pubic region, the penis is again rotate to assume a vertical orientation, and the rod can be pushed upward.

It should be noted that the patient's ability to manipulate and move the rod is brought about by the fact that the second portion 408b of the sleeve is well lubricated and implanted under the skin and above the deep or superficial fascia.

Reference in now made to FIG. 17, which is a schematic drawing illustrating an embodiment of the present invention, in which the device 400 of FIG. 11 includes a perforated enclosure 304 joined to an outer surface of the portion of the sleeve implanted in the penis shaft and/or a plurality of loops 120 joined to an outer surface of the portion of the sleeve implanted in the penis shaft. The perforated enclosure 304, as well as the reservoir 300 and conduit 308 associated therewith have been described in FIG. 6. The loops 120 have been described in FIG. 2. The loops 120 are configured for tying the device 400 to a suture, if needed.

In a variant, the perforated enclosure 304 is joined to the sleeve 408 on both sides of the curved base frame. The perforated enclosure 304 is fusedly connected to the sleeve 408, and thus traverses the tube 406. Optionally, the conduit 308 is joined to the perforated enclosure 304 in the vicinity of the tube 406 (thus, near the base of the penis). Thus, it is possible to deliver the fluid from the reservoir 300 to a section of the perforated enclosure 304 joined to the first portion 408a (and thereby to the penis root in the example of FIGS. 13 and 14), to a section of the perforated enclosure 304 joined to the second portion 408b (and thereby to the penis shaft in the example of FIGS. 13 and 14), or to both sections of the perforated enclosure 304. This can be done by tilting the second portion 408b (the penis shaft) upward, downward, or horizontally to direct the incoming fluid to the desired location(s). Also, pressing on the section of the perforated enclosure 304 joined to the second portion 408b can be used to decrease or eliminate the flow of the fluid to the section of the perforated enclosure 304 joined to the second portion 408b, and direct most of the fluid to the section of the perforated enclosure 304 joined to the first portion 408a.

Figure 18:
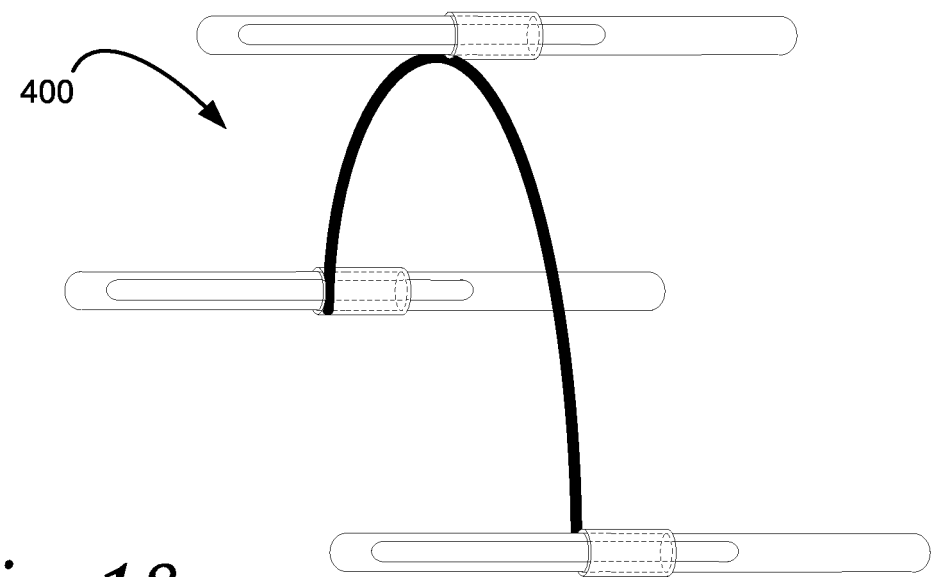
FIG. 18 is a schematic drawing illustrating an embodiment of the present invention, in which the device of FIG. 11 includes at least three rods.

Reference in now made to FIG. 18, which is a schematic drawing illustrating an embodiments of the present invention, in which the device 400 of FIG. 11 includes at least three rods.

In FIG. 18, an additional tube-sleeve-rod assembly as described above is joined to the wire-like curved base frame along the curve delineated by the wire-like curved base frame.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. An implant for helping a male patient achieve a penile erection, the implant comprising a pair of substantially straight and substantially rigid rods and an interconnecting structure, wherein:
   the rods are configured for being implanted subcutaneously in the patient and are selectively movable from a retracted mode of the implant to a deployed mode of the implant, where in the deployed mode the rods are within the penis shaft and in the retracted mode at least a majority of each rod is out of the penis shaft; and
   the interconnecting structure is implanted subcutaneously in the patient and joined to the rods, and is configured for stabilizing the rods within the penis shaft.

2. The implant of claim 1, wherein the interconnecting structure is configured for moving with the rods.

3. The implant of claim 1, wherein the interconnecting structure is configured for being substantially static.

4. A device for helping a male patient achieve a penile erection, the device comprising the implant of claim 2 and a sealed, hollow, flexible sheath, wherein:
   the implant of claim 2 is in a form of a rod unit which comprises the rods and a substantially rigid curved section having a first and a second end, the curved section forming the interconnecting device and each rod of the rods being joined to a respective end of the curved section and extending away from the curved section at non-zero angle with a plane which includes the curved section;
   the rods extend away from the curved section essentially in the same direction;
   the sheath is configured for enclosing the rod unit, and comprises a body portion, and two thin elongated legs extending away from one side the body portion;
   the body portion is configured for enclosing at least a majority of the rod unit when the rod unit is retracted within the body portion, and the legs are configured for enclosing the rods when the rod unit is deployed out of the body portion; and
   the rod unit is selectively movable from a retracted mode thereof to a deployed mode thereof, where in the retracted mode at least a majority of the rod unit is within the sheath's body part, and in the deployed mode the rods are enclosed in the respective legs of the sheath.

5. The device of claim 4, wherein:
   the body portion is configured for being subcutaneously implanted in the patient's pubic region above the patient's penis, and the legs are configured for being implanted along sides of a shaft of the patient's penis below a skin of the penis and above a deep or superficial fascia of the penis;
   the rod unit is selectively movable from the retracted mode thereof to the deployed mode thereof, where in the retracted mode the rod unit does not extend along the penis shaft, and in the deployed mode the curved section holds a base of the penis and stabilizes the rods while the rods are enclosed in the respective legs of the sheath and thus provide rigidity of the penis shaft.

6. The device of claim 4, wherein the non-zero angle between rods and the plane which includes the curved section is between about 60 degrees and 120 degrees.

7. The device of claim 4, wherein the curved section is somewhat flexible.

8. The device of claim 4, wherein the sheath comprises and encloses lubricant material.

9. The device of claim 4, comprising at least one loop joined to an outer surface of at least one leg of the sheath.

10. The device of claim 4, wherein the curved section of the rod is configured for being located in a vicinity of a suspensory ligament of the penis, when the rod unit is in the deployed mode.

11. The device of claim 4, further comprising:
a hollow reservoir configured for being implanted in the patient's body, and for receiving and holding a fluid;
a conduit having a first end in fluid communication with the hollow reservoir and a second end;
a perforated enclosure joined to an outer surface of at least one leg and extending along a length of the at least one leg, the perforated enclosure being in fluid communication with the conduit's second end and having at least one opening configured for releasing the fluid delivered to the perforated enclosure from the reservoir via the conduit into the patient's body.

12. The device of claim 11, comprising a valve at a junction between the reservoir and the conduit, the valve being configured for enabling the fluid's flow from the reservoir to the conduit, when at least a predetermined pressure is exerted on the reservoir.

13. The device of claim 4, wherein the rod unit comprises two sections removably joinable to each other, the first section comprising a first portion of the curved section and a first one of the rods and the second section comprising a second portion of the curved section and a second one of the rods, such that the first portion of the curved section is removably joinable to the second portion of the curved section.

14. The device of claim 4, wherein the rod unit comprises plurality of rods substantially parallel to each other and joined to the curved section.

15. The device of claim 14, wherein the sheath comprises a plurality of legs, each leg being configured for enclosing a respective one of the rods.

16. A device for being implanted in a body of the patient and for helping a male patient achieve a penile erection, the device comprises the implant of claim 3 and two sealed flexible sleeves, wherein:
the implant of claim 3 comprises the pair of rods and the interconnecting structure, the interconnecting structure comprising a curved base frame and two tubes;
the curved base frame is substantially rigid and has two ends;
each tube is joined to the curved base frame near a respective end of the curved base frame, and extends away from the curved base frame, the tubes being at a non-zero angle with a plane which includes the curved base frame;
each tube is traversed by a respective one of the flexible sleeves;
each sleeve encloses a respective one of the rods; and
each rod is selectively movable within the respective sleeve between a rear side of the curved base frame and a front side of the curved base frame.

17. The device of claim 16, wherein:
the curved base frame is configured for being implanted in a pubic region in a vicinity of a base of a penis of the patient, to encircle a portion a base of a penis of the patient, and for being implanted below a skin of the penis and above or within a suspensory ligament of the penis;
each tube is implanted below the skin in a vicinity of the penis base;
a first portion of each sleeve on the rear side of the curved base frame is configured for being implanted along a root of the penis or below a skin on a pubic area of the patient;
a second portion of each sleeve on the front side of the curved base frame is configured for being implanted along a shaft of the patient's penis;
each rod is selectively movable within the sleeve between the rear side of the curved base frame and the front side of the curved base frame, such that the rods provide rigidity to the penis shaft when located in the front portions of the respective sleeves.

18. The device of claim 16, wherein the curved base frame is somewhat flexible.

19. The device of claim 16, wherein at least one of the sleeves comprises and encloses lubricant material.

20. The device of claim 16, comprising at least one loop joined to an outer surface of at least sleeve on the front side of the curved base frame.

21. The device of claim 16, further comprising:
a hollow reservoir configured for being implanted in the patient's body, and for receiving and holding a fluid;
a conduit having a first end in fluid communication with the hollow reservoir and a second end;
a perforated enclosure joined to an outer surface of at least one sleeve and extending along at least part of a length of the at least one sleeve, the perforated enclosure being in fluid communication with the conduit's second end and having at least one opening configured for releasing the fluid delivered to the perforated enclosure from the reservoir via the conduit into the patient's body.

22. The device of claim 21, comprising a valve at a junction between the reservoir and the conduit, the valve being configured for enabling the fluid's flow from the reservoir to the conduit, when at least a predetermined pressure is exerted on the reservoir.

23. The device of claim 16, comprising:
a plurality of tubes, each joined to the curved base frame;
a plurality of sleeves, each traversing a respective tube; and
a plurality of rods, each enclosed within a respective sleeve.

* * * * *